United States Patent [19]

Fischer

[11] Patent Number: 4,491,728
[45] Date of Patent: Jan. 1, 1985

[54] DEVICE FOR DETECTING DEFECTS IN GLASS ARTICLES

[75] Inventor: Knut Fischer, Auetal, Fed. Rep. of Germany

[73] Assignee: Hermann Heye, Obernkirchen, Fed. Rep. of Germany

[21] Appl. No.: 363,133

[22] Filed: Mar. 29, 1982

[30] Foreign Application Priority Data

Apr. 9, 1981 [DE] Fed. Rep. of Germany ....... 3114285

[51] Int. Cl.³ ............................................. G01N 21/32
[52] U.S. Cl. .................................. 250/223 B; 356/240
[58] Field of Search ............................ 250/223 B, 560; 356/240, 376, 392; 209/525

[56] References Cited

U.S. PATENT DOCUMENTS

| | | | |
|---|---|---|---|
| 2,174,848 | 10/1939 | Stahmer | 356/240 |
| 2,645,971 | 7/1953 | Herbst | 356/376 |
| 3,089,594 | 5/1963 | Early | 250/223 B |
| 3,245,533 | 4/1966 | Rottmann | 356/240 |
| 3,529,169 | 9/1970 | Heaney et al. | 250/223 B |
| 3,549,890 | 12/1970 | Keller | 209/525 |
| 3,625,618 | 12/1971 | Bickel | 356/376 |
| 4,213,042 | 7/1980 | Beach et al. | 250/223 B |
| 4,259,571 | 3/1981 | Dubberly | 250/223 B |

Primary Examiner—David C. Nelms
Assistant Examiner—Ernest Austin, II
Attorney, Agent, or Firm—Michael J. Striker

[57] ABSTRACT

A device for detecting unacceptable defects in a neck area of hollow glass articles transported by a feeding element has a light source spaced from a path of feeding of the articles and arranged to illuminate the neck area of the latter, a projecting element arranged to project an image of the neck area of each of the glass articles, an image receiving element arranged to receive the projected image of the neck area and having a plurality of electrooptical elements, wherein the projecting element includes a mirror arranged to project the image of the neck area of each of the articles along a projecting axis which is transverse to the longitudinal axis of the device, and the electrooptical elements are arranged in a circle located in a plane normal to the projecting axis.

14 Claims, 5 Drawing Figures

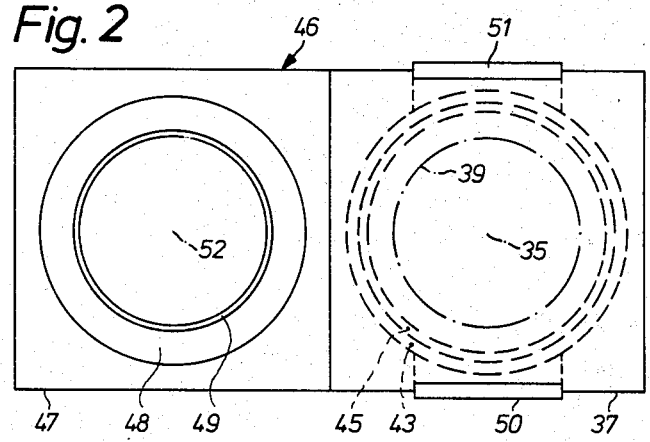
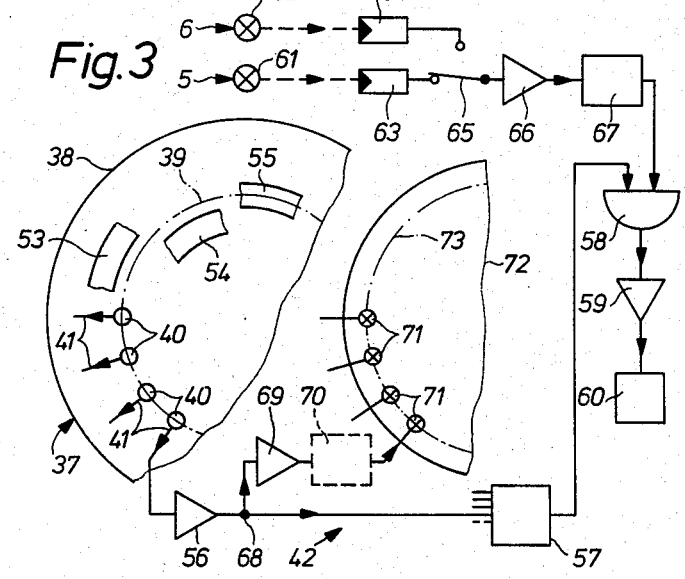
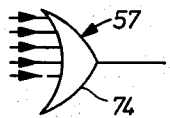
Fig. 4
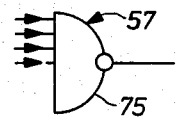
Fig. 5

DEVICE FOR DETECTING DEFECTS IN GLASS ARTICLES

BACKGROUND OF THE INVENTION

The present invention relates in general to a device for detecting unacceptable defects in hollow glass articles. Devices of the above-mentioned general type are known in the art. One known device is disclosed, for example, in the German Offenlegungsschrift No. 29 16 361. In this device a light source is formed by a plurality of flashlights which are arranged in a circle coaxial with a test piece located in a measuring position. In each testing cycle, all flashlights are simultaneously actuated by a light barrier reacting to the presence of the test piece, and they are actuated in a single action. The flash beam passes through a ring-shaped dispersion disk located outwardly of an image tube and partially impinges on the top surface of the mouth or neck of the test piece. From there a portion of the light beam is reflected into the interior of the image tube and received by a television camera arranged at the upper end of the image tube and operating in accordance with a light-scanning method. Thereby a charge image is formed on a light-sensitive layer of the tube of the television camera, which corresponds to the image of the upper surface of the neck of the glass article. This charge image is stored and later on is evaluated in an interpreting circuit. Until then, the scanning beam of the camera tube must be blocked to prevent a premature extinction of the stored charge image. From the pairs of pulses resulting during the line-by-line scanning of the charge image, chordal length signals are produced and compared with nominal value signals. If a deviation from a preset value is detected, a fault signal is generated and used for actuation of an ejector. The devices for producing, visualization, and interpreting of these fault signals are relatively uncertain and complicated and can be serviced and repaired by specially trained staff which is normally not available in glassworks, particularly in developing countries. This staff is not readily available, as compared with the conventional staff in the glassworks, to accept indispensible late, and night shifts. Moreover, the known testing device can detect only a defective sealing face of the neck of glass articles.

The pamphlet "Kombi-Inspektor Typ 64" 3000 d.9/77 of Hermann Kronseder, Maschinenfabrik, D-8402 Neutraubling, describes a bottom inspection of bottles. The bottles are illuminated by an illuminating device from below. Beams pass through the neck of the bottle and optical means in a light divider, and the latter deflects a part of the beam at a right angle and deflects it through optical means onto a hexagonal flat light-emitting diode array for inspecting the bottle bottom center.

SUMMARY OF THE INVENTION

Accordingly, it is an object of the present invention to provide a device for detecting defects in a neck area of hollow glass articles, which avoids the disadvantages of the prior art.

More particularly, it is an object of the present invention to provide a device for detectings defects in a neck area of glass articles which is simpler in construction and for service and repair and which can be understood and maintained by a not specially trained staff.

It is another object of the present invention to provide a device for detecting defects in a neck area of glass articles, which makes possible reducing of operational expenditures.

It is also an object of the present invention to provide a device for detecting defects in a neck area of glass articles, in which in addition to detection of defective sealing faces resulting, for example from split-glass and not fully pressed or blown necks, also other defects can be detected, such as a wobble defect (parallel and/or angular and/or warped offset of the longitudinal axes of the neck and the bottom relative to one another), strong saddle formation, ovality, strong dirtying by mold lubricants, necks inclined relative to a horizontal, picks, overpressed necks, and the defect known as "line over finish", wherein detection of the defects is basically independent from the type of the neck.

In keeping with these objects and with others which will become apparent hereinafter, one feature of the present invention resides, briefly stated, in a device for detecting unacceptable defects in a neck area of hollow glass articles which has means for continuously feeding glass articles along a predetermined path, detecting means having a longitudinal axis, a light source spaced from the path of feeding of the articles and arranged to illuminate the neck area of each of the articles, a projecting element arranged to project an image of the neck area of each of the glass articles, an image receiving element arranged to receive the projected image of the neck area of each of the glass articles and having a plurality of electrooptical elements connected with interpreting means connected to an ejector, wherein the projecting element includes a mirror arranged to project the image of the neck area along a projecting axis which is transverse to the longitudinal axis of the detecting means, and the electrooptical elements are arranged in a circle located in a plane normal to the projecting axis.

When the device for detecting is designed in accordance with these features, it attains the above-mentioned objects. The deflection of the neck image by the mirror considerably facilitates and improves the visual adjustment of the testing device. The dimensions and the number of electrooptical elements arranged in a circle of a predetermined diameter makes possible to provide each desirable sensitivity of the defect-detecting process. The sensitivity of the defect detection is also further influenced by the adjustment of the neck image relative to the electrooptical elements.

In accordance with another feature of the present invention, an objective is located between the neck areas of the glass articles transported by respective means, and the mirror, and the objective is adjustable relative to the mirror. These features serve for adjusting the device for different testing tasks with different neck diameters. The objective may advantageously be formed as an achromatic objective composed of two bonded lenses.

Still another feature of the present invention is that the mirror and the objective are arranged in a common image tube. This facilitates mounting and shields the optical system from undesirable dispersion light.

The light-receiving element may be adjustable along the projecting axis relative to the mirror. The device can thereby be adjusted, particularly for readjustment to different types of glass articles and readjustment for detection of different types of defects, for example from detection of defective sealing face to detection of a wobble defect.

A further feature of the present invention is that the electrooptical elements are supported on a supporting plate which is formed as a ground-glass plate. This facilitates the operation of the device inasmuch as all electrooptical elements can be retained in their place during the adjustment of the detecting device.

Alternately, the receiving element and the ground-glass plate can be exchanged, for example by a slider for adjusting and subsequent testing operation.

In accordance with a further feature of the present invention, the light source includes an adjustable lamp, followed by at least one collector lens and a condenser lens, and the mirror is located between the collector lens and the condenser lens so that the image of neck area is projected through a central opening of the condenser lens onto the mirror. A commercially used H3 halogen lamp can be utilized here, as known in auto headlights. These lamps are easy to exchange when needed. A flashlight device is not necessary for the light source in accordance with the invention. At least one collector lens and the condenser lens can be mounted in a simple and clear manner in an illumination tube. The arrangement of the mirror between the convex faces of the lenses is very space-economical and facilitates beam guidance of the system.

A next feature of the invention is that the image tube is located in the central through opening of the condenser lens. This provides for an especially simple, distortionless and compact construction. The image tube can be glued in the opening of the condenser lens.

Another feature of the present invention is that the detecting means is arranged so that in the event of wobble defect detection the image of the neck area exhibiting at most an acceptable axis deviation is located in the regions of the image receiving element outside or inside of the electrooptical elements, whereas in the event of unacceptable axis deviation at least one of the electrooptical elements is illuminated by the image of the neck area. This provides for an especially reliable and simple detection of the wobble defects. The initially adjusted radial distance between the neck image and the electrooptical elements influences the tolerance of the detection of the wobble defect.

A further feature of the present invention is the fact that the detecting means is arranged so that in the event of detection of defective sealing faces of the neck areas of the glass articles, all electrooptical elements are illuminated by the image of the sealing faces, exhibiting at most acceptable defects, whereas in the event of an unacceptable defect of the sealing faces at least one of the electrooptical elements is not illuminated. This guarantees a reliable detection of the defective sealing faces.

The interpreting means may include a plurality of input amplifiers each connected with a respective one of the electrooptical elements, a logic element having a plurality of inputs each connected with a respective one of the input amplifiers and an output connected by an AND-gate and an output amplifier with the ejector; and a further receiving element, a further amplifier connected with the further receiving element, and a first monostable flip-flop connects the further receiving element with the AND-gate. The thus designed interpreting means is relatively simple and provides for, in contrast to the discussed prior art, parallel interpretation of the outputs of all electrooptical elements. In dependence upon the type of the logic element, different types of defects, for example defective sealing face or wobble defect, can be evaluated by a simple reprogramming.

Signalling means may further be provided including a plurality of signal lamps, and a post-amplifier connecting a point between the input amplifier and the respective one of the inputs of the logic element with a respective one of the signalling lamps. A monostable flip-flop may connect each of the post-amplifiers with a respective one of the signalling lamps. The thus-designed detecting device provides for an optical checking of the spatial location and indication of the defects during adjustment of the device.

The signal lamps may be arranged on an inspection or display panel in a circle in correspondence with the electrooptical elements of the detecting means. This facilitates the optical checking of the defects.

The logic element for detecting wobble defects may be formed as an OR-gate or as a NAND-gate. Thereby, a particular type of the logic element is suitable for detection of a predetermined type of defects. The logical element of these different types can be arranged, for example on a plug-in card and therefore easily exchangeable during reprogramming.

The novel features which are considered as characteristic for the invention are set forth in particular in the appended claims. The invention itself, however, both as to its construction and its method of operation, together with additional objects and advantages therof, will be best understood from the following description of specific embodiments when read in connection with the accompanying drawing.

BRIEF DESCRIPTION OF THE DRAWING

FIG. 2 is a lateral view of a part of the device in accordance with another embodiment of the invention;

FIG. 3 is a diagram of an electronic interpreting circuit for the detecting device; and FIGS. 4 and 5 show different types of logic elements for detection of different defects.

DESCRIPTION OF THE PREFERRED EMBODIMENTS

Figure 1:
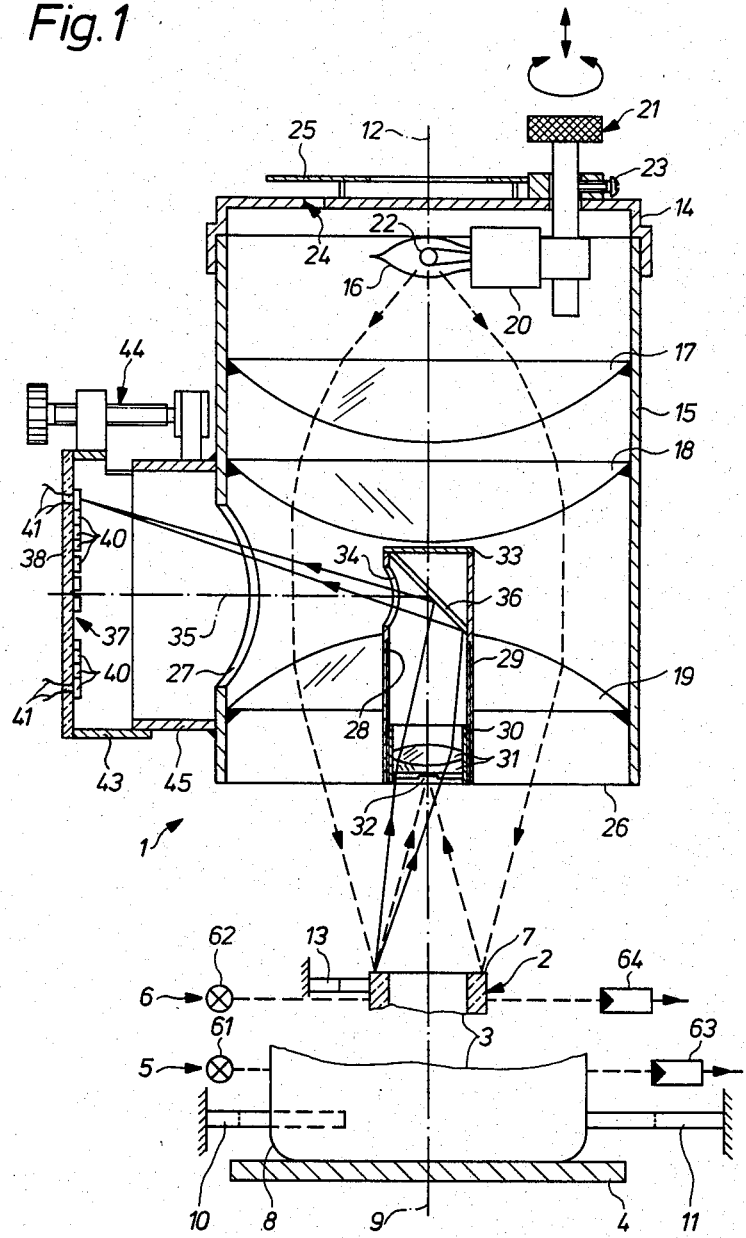
FIG. 1 is a longitudinal view of a device for detecting defects in a neck area of glass articles in accordance with the present invention.

A device for detecting not-acceptable defects in neck areas of glass articles has a detecting part which is identified by reference number 1 in FIG. 1. A test piece 3 has a mouth or neck or finish 2 and is formed as a hollow glass article, here a bottle.

The test piece 3 is arranged on a schematically-shown transporting chain 4 which moves normal to the plane of the drawing in advantageously continuous operation. The test pieces 3 are arranged on the transporting chain 4 generally one behind the other in the transporting direction. The distance between the successive test pieces 3 from one another is not critical since each test piece 3 actuates its own detection cycle by a starting light barrier 5 or 6.

The invention is described hereinbelow with regard to two characteristic types of defects, namely the wobble defect and the defective sealing face 7 of the neck 2. The "sealing face" 7 is the upper limiting face of the neck 2 independent of the respective type of the neck.

During detection of the wobble defect it is determined whether the eccentricity of the neck 2 relative to a longitudinal axis 9 of a bottom 8 of the test piece 3 is located within or without predetermined tolerances.

The test piece 3 is centered on the transporting chain 4 first by a centering rail 10 at one side of the transporting chain 4, and subsequently by a centering rail 11 at the other side of the transporting chain 4 transverse to the transporting direction, into its transverse position in FIG. 1. The centering rails 10 and 11 are fixedly mounted on a not-shown frame of the detecting device and cooperative with the region of the bottom 8 of the test piece 3. For detecting the wobble defect, a further centering of the test piece 3 in the testing position shown in FIG. 1 does not take place, and the testing cycle is activated by the lower starting light barrier 5. In this testing position in which the starting light barrier 5 is rendered dark by the test piece 3, the longitudinal axis 9 of the bottom 8 coincides with a longitudinal axis 12 of the testing device 1.

When it is necessary to determine whether a not-acceptable defect takes place on the sealing face 7, the above-described transverse centering of the approaching test piece 3 by the centering rails 10 and 11 prior to the testing position takes place as coarse centering. After this, an additional fine centering by a fine centering rail 13 engaging the neck 2 takes place. In this case, the starting light barrier 6 is exclusively used instead of the starting light barrier 5, in cooperation with the neck 2.

The detecting device 1 has an illuminating tube 15 closeable by a cover 14, and a lamp 16, collector lenses 17 and 18, a condenser lens 19 arranged in the tube 15. The lamp 16 is seated in a mount 20. The mount 20 can be centered in two directions by an adjusting device 21 supported on the cover 14, so that finally a spiral 22 of the lamp 16 lies in the longitudinal axis 12 of the detecting device 1. For influencing the illumination of the neck 2, the spiral 22 can be adjusted by the adjusting device 21 in direction of the longitudinal axis 12 and secured by an arresting screw 23.

A plurality of ventilating openings 24 is provided in the cover 14 and distributed over its periphery, a shielding plate 25 is mounted above the ventilating openings on the cover 14. The tube 15 has a lower opening 26 and a lateral opening 27.

The condensor lens 19 is provided with a central opening 28, and a central part of an image tube 29 is glued in the opening 28. The image tube 29 has an inner thread in which a mounting ring 30 for an objective 31 is screwed via key groves 32 in a desired axial position. The objective 31 is an achromatic objective composed of two lenses glued together. The tube 29 is closed from above by a cover 33 and has a lateral opening 34 adjacent to the cover. The opening 34 is in alignment with the lateral opening 27 of the illumination tube 15 along a projection axis 35. A mirror 36 is fixedly arranged in the tube 29 so that the center of the mirror is located in a crossing point of the projection axis 35 with the longitudinal axis 12. The mirror 36 projects the image from the objective 31 through the lateral openings 34 and 27 onto an electrooptical receiver 37.

The receiver 37 has a supporting plate 38 formed as a ground-glass plate, and a plurality of electrooptical elements 40 which are mounted on the supporting plate 38 and more particularly at its side facing toward the mirror 36. The electrooptical elements 40 are arranged in a circle 39. The circle 39 lies in a plane which is normal to the projection axis 35. Each electrooptical element 40 is connected by a conductor 41 with an electronic interpreting circuit 42 as can be seen from FIG. 3.

The receiver 37 is mounted on a ring 43 which can be adjusted by an adjusting device 44 along the projection axis 35 relative to a pipe 45 mounted on the tube 15.

In the embodiment shown in FIG. 2, the receiver 37 is a component of a slider 46 in which a circular ground-glass disk 48 is inserted in a section 47 adjoining the receiver 37. The ground-glass disk 48 is provided with a double circle marking 49 whose center circle corresponds to the circle 39 of the electrooptical elements 40. Other marks can be provided on the ground-glass disk 48 for adjusting the detecting device 1.

The slider 46 is laterally displaceable in guiding elements 50 and 51 mounted on the ring 43. Other parts of the detecting device 1 are omitted in FIG. 2 for the sake of simplification. For adjusting, the slider 46 is displaced to the right in FIG. 2, until a center 52 of the ground-glass disk 48 is located in the projection axis 35. Then a standard glass article with at most acceptable neck defects is moved on the stationary transporting chain 4 until the image of the neck 2 is brought on the ground-glass disk 48 in the desirable relative position to the double circle marking 49. After this, the centering rails 10, 11, 13 and the starting light barriers 5 or 6 are adjusted. If necessary, the entire testing device 1 can be displaced in direction of its longitudinal axis 12 relative to the transporting chain 4. When the adjustment of the image of the neck 2 of the ground-glass disk 48 is completed, the slider 46 is displaced to the shown testing position in FIG. 2, in which the center of the circle 39 lies on the projection axis 35.

FIG. 3 illustrates detection of the wobble defect, wherein an image 53 of the neck 2 is located outside and alternately another image 54 of the neck 2 is located inside and at a radial distance from the circle 39. This radial distance defines a tolerance zone for the determination of a not-acceptable defect. When the image 53 or 54 with decrease of the radial tolerance zone sufficiently approaches the electrooptical elements 40, at least one electrooptical element 40 is illuminated and produces a fault signal conveyed via its conductor 41 to the interpreting circuit 42.

During detection of a defective sealing face 7, an image 55 of the sealing face 7 containing at most acceptable defects is located directly on the circle 39, so that all electrooptical elements 40 are illuminated. When a neck possesses a not-acceptable defect in the sealing face 7, at least one of the electrooptical elements 40 is not illuminated by the image 55. This defect information is conveyed via the associated conductor 41 to the interpreting circuit 42.

In the interpreting circuit 42, each conductor 41 is connected via an input amplifier or a preamplifier 56 with an individual input of a logic element 57 whose output is connected via an AND-gate 58 and an output or end-amplifier 59 with an expeller 60.

The starting light barriers 5 and 6 have respectively a light source 61 and 62 and a receiver 63 and 64. The receivers 63 and 64 are connected via a selective switch 65 selectively via an amplifier 66 and a first monostable flip-flop 67 with a further input of the AND-gate 58.

A point 68 between each pre-amplifier 56 and the associated input of the logical element 57 is connected with a signal lamp 71 via a post-amplifier 69 and sometimes via a subsequent second monostable flip-flop 70. The signal lamps 71 are arranged on a display panel 72 in a circle 73 with a sequence which corresponds to the respective electrooptical element 40.

The logic element 57 shown in FIG. 4 is formed as an OR-gate 74 and serves for detection of wobble defects. The logic element 57 shown in FIG. 5 is formed as a NAND-gate 75 and used for detection of a defective sealing face 7.

It will be understood that each of the elements described above, or two or more together, may also find a useful application in other types of constructions differing from the types described above.

While the invention has been illustrated and described as embodied in a device for detecting defects in neck areas of glass articles, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A device for detecting unacceptable defects in a neck area of glass articles, comprising means for continuously feeding glass articles in a substantially upright position without rotation about their longitudinal axis along a predetermined path; detecting means having a longitudinal axis, a stationary light source spaced from the path of feeding of the articles and located above the neck areas of the glass articles so as to illuminate the neck area of each of the articles, an objective through which an image of the neck area of each of the glass articles is projected, a mirror located above the neck area of of the glass articles so that said objective is located between the neck areas of the glass articles and said mirror, so as to project the image projected through said objective by said mirror along a projecting axis which is transverse to said longitudinal axis, an image receiving element arranged to receive the image of the neck area of each of the glass articles projected by said mirror and having a plurality of electrooptical members arranged in a circle, and said electrooptical members being located in a plane normal to said projecting axis; and interpreting means connected with said electrooptical members and arranged to actuate an article ejector.

2. A device as defined in claim 1, wherein said objective is adjustable relative to said mirror; and further comprising means for adjusting said objective relative to said mirror.

3. A device as defined in claim 1, wherein said detecting means has an image tube, said mirror and said objective being arranged in said image tube.

4. A device as defined in claim 1, wherein said receiving element is adjustable along said projecting axis relative to said mirror, said detecting means further including means for adjusting said receiving element relative to said mirror along said projecting axis.

5. A device as defined in claim 1, wherein said detecting means further includes a supporting plate which supports said electrooptical element and is formed as a ground-glass plate.

6. A device as defined in claim 5, wherein said receiving element is replaceable by a ground-glass plate.

7. A device as defined in claim 1, wherein said light source includes an adjustable lamp, at least one collector lens downstream of said lamp, and at least one condenser lens downstream of said collector lens, said mirror being located between said collector lens and said condensor lens, and the latter having a central through opening through which the image of the neck area is projected via said mirror onto said image-receiving element.

8. A device as defined in claim 7, wherein said detecting means further has an image tube located in said central through opening of said condenser lens, an objective and said mirror being arranged in said image tube.

9. A device as defined in claim 1, wherein said detecting means is arranged so that in the event of wobble defect detection, the image of the neck area exhibiting at most an acceptable parallel and/or angular and/or warped offset of the longitudinal axis of the neck relative to the longitudinal axis of a bottom of the glass article, is located in the regions of the image receiving element outside or inside of said electrooptical elements, whereas in the event of unacceptable axis offset at least one of said electrooptical elements is illuminated by the image of the neck area.

10. A device as defined in claim 9, wherein said interpreting means includes a plurality of input amplifiers each connected with a respective one of said electrooptical elements, and a logic element having a plurality of inputs each connected with a respective one of said input amplifiers and an output connected with the ejector, said logic element being formed as an OR-gate.

11. A device as defined in claim 1, wherein said detecting means is arranged so that in the event of detection of defective sealing faces of the neck areas of the glass articles, all electrooptical elements are illuminated by the image of the sealing faces, exhibiting at most acceptable defects, whereas in the event of an unacceptable defect of the sealing faces at least one of said electrooptical elements is not illuminated.

12. A device as defined in claim 11, wherein said interpreting means includes a plurality of input amplifiers each connected with a respective one of said electrooptical elements, and a logic element having a plurality of inputs each connected with a respective one of said input amplifiers and an output connected with the ejector, said logic element being formed as a NAND-gate.

13. A device as defined in claim 1, wherein said interpreting means includes a plurality of input amplifiers each connected with a respective one of said electrooptical members, a logic element having a plurality of inputs each connected with a respective one of said input amplifiers and an output, and an AND-gate with an output amplifier connecting said output of said logic element with the ejector; and further comprising detection actuating means connected with said AND-gate and including a light-barrier having a further receiving element, a further amplifier connected with said further receiving element, and a first monostable flip-flop connecting said further receiving element with said AND-gate; and defect signalling means including a plurality of signal lamps, a post-amplifier connecting a point between said input amplifier and a respective one of said inputs of said logic element with a respective one of said signalling lamps, and a further monostable flip-flop connecting each of said post-amplifiers with a respective one of said signalling lamps.

14. A device as defined in claim 13, wherein said signalling means includes a display panel, said signal lamps being arranged on said display panel in a circle in correspondence with said electrooptical elements of said detecting means.

* * * * *